(12) United States Patent
Komplin et al.

(10) Patent No.: US 7,385,090 B2
(45) Date of Patent: Jun. 10, 2008

(54) METHOD OF TREATING AN ALDEHYDE MIXTURE, USE OF THE TREATED ALDEHYDE, AND AN ALCOHOL

(75) Inventors: Glenn Charles Komplin, Katy, TX (US); Joseph Broun Powell, Houston, TX (US); Paul Richard Weider, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/669,694

(22) Filed: Jan. 31, 2007

(65) Prior Publication Data

US 2007/0179322 A1 Aug. 2, 2007

Related U.S. Application Data

(60) Provisional application No. 60/763,985, filed on Feb. 1, 2006, provisional application No. 60/820,900, filed on Jul. 31, 2006.

(51) Int. Cl.
*C07C 45/78* (2006.01)
*C07C 31/18* (2006.01)
(52) U.S. Cl. ................. 568/492; 568/852; 568/862
(58) Field of Classification Search .................. None
See application file for complete search history.

(56) References Cited

U.S. PATENT DOCUMENTS

| | | | |
|---|---|---|---|
| 2,779,794 A | 1/1957 | Catterall | 260/604 |
| 3,868,422 A | 2/1975 | Hart et al. | 260/604 |
| 3,966,886 A | 6/1976 | Bakker | 423/417 |
| 4,041,057 A | 8/1977 | Fanning | 260/410.9 R |
| 4,145,486 A | 3/1979 | Haag et al. | 521/31 |
| 4,161,616 A * | 7/1979 | Taylor et al. | 568/862 |
| 4,234,545 A | 11/1980 | El-Chahawi et al. | 423/138 |
| 4,365,071 A | 12/1982 | Yamanis | 549/377 |
| 4,625,067 A | 11/1986 | Hanin | 568/451 |
| 4,654,445 A | 3/1987 | Ono et al. | 568/454 |
| 5,237,105 A | 8/1993 | Summerlin | 568/451 |
| 5,414,100 A | 5/1995 | Ayorinde et al. | 554/191 |
| 5,451,384 A | 9/1995 | Carr | 423/210 |
| 5,457,240 A | 10/1995 | Beadle et al. | 568/451 |
| 5,463,144 A | 10/1995 | Powell et al. | 568/867 |
| 5,463,145 A | 10/1995 | Powell et al. | 568/867 |
| 5,463,146 A | 10/1995 | Slaugh et al. | 568/862 |
| 5,504,261 A | 4/1996 | Mullin et al. | 568/862 |
| 5,545,765 A | 8/1996 | Slaugh et al. | 568/862 |
| 5,545,766 A | 8/1996 | Powell et al. | 568/862 |
| 5,545,767 A | 8/1996 | Weider et al. | 568/867 |
| 5,563,302 A | 10/1996 | Weider et al. | 568/862 |
| 5,576,471 A | 11/1996 | Semple et al. | 568/862 |
| 5,585,528 A | 12/1996 | Powell et al. | 568/862 |
| 5,689,016 A | 11/1997 | Weider et al. | 568/862 |
| 5,723,389 A | 3/1998 | Slaugh et al. | 468/862 |
| 5,731,478 A | 3/1998 | Slaugh et al. | 568/862 |
| 5,777,182 A | 7/1998 | Powell et al. | 568/862 |
| 5,786,524 A | 7/1998 | Powell et al. | 568/862 |
| 5,841,003 A | 11/1998 | Slaugh et al. | 568/867 |
| 5,981,808 A | 11/1999 | Powell et al. | 568/862 |
| 5,986,145 A | 11/1999 | Powell et al. | 568/449 |
| 6,130,351 A | 10/2000 | Stern et al. | 562/17 |
| 6,165,428 A | 12/2000 | Eijkhoudt et al. | 423/210 |
| 6,323,374 B1 | 11/2001 | Han | 568/483 |
| 6,376,720 B1 | 4/2002 | Han | 568/483 |
| 6,376,724 B1 | 4/2002 | Han | 468/861 |
| 6,403,836 B2 | 6/2002 | Kaizik et al. | 568/451 |
| 6,657,078 B2 | 12/2003 | Scates et al. | 562/519 |
| 6,660,892 B2 | 12/2003 | Powell et al. | 568/867 |
| 6,684,214 B2 | 1/2004 | Bata et al. | 707/10 |
| 6,911,566 B2 * | 6/2005 | Tsunoda et al. | 568/862 |
| 2002/0151746 A1 | 10/2002 | Scates et al. | 562/519 |
| 2003/0032845 A1 | 2/2003 | Han et al. | 568/862 |
| 2004/0087819 A1 | 5/2004 | Powell et al. | 568/862 |
| 2005/0020805 A1 | 1/2005 | Sunkara et al. | 528/425 |
| 2005/0069997 A1 | 3/2005 | Adkesson et al. | 435/158 |
| 2005/0127003 A1 | 6/2005 | Dennis | 210/662 |

FOREIGN PATENT DOCUMENTS

| | | |
|---|---|---|
| DE | 1965440 | 8/1970 |
| EP | 713852 | 5/1996 |
| GB | 2055371 | 3/1981 |
| JP | 2004-182622 | 2/2004 |
| SU | 994461 | 2/1983 |
| WO | WO199324437 | 12/1993 |
| WO | WO199422563 | 10/1994 |
| WO | 1997/16250 | 5/1997 |

(Continued)

OTHER PUBLICATIONS

S.A. Miller et al., "Liquid-Solid Systems", Perry's Chemical Engineer's Handbook, 6th ed.. (McGraw-Hill 1984), pp. 19-40 to 19-45.

(Continued)

*Primary Examiner*—Sikarl A. Witherspoon

(57) ABSTRACT

A method of treating an aldehyde mixture comprising a carboxylic acid and a metal cation, which method comprises: contacting the aldehyde mixture with a basic separating medium, and subsequently or simultaneously contacting with an acidic separating medium; use of the treated aldehyde mixture to prepare an alcohol; and the alcohol.

24 Claims, 1 Drawing Sheet

FOREIGN PATENT DOCUMENTS

| WO | 1997/33851 | 9/1997 |
|---|---|---|
| WO | WO20014041 | 3/2000 |
| WO | 2001/09069 | 2/2001 |
| WO | WO200109069 | 2/2001 |
| WO | 2002/06393 | 1/2002 |
| WO | WO2004031108 | 4/2004 |

OTHER PUBLICATIONS

R. Weber et al., "Hydroformylation of epoxides catalyzed by cobalt and hemilabile P-O Ligands", Chem. Commun., (2000) pp. 1419-1420.

Kirk-Othmer Encyclopedia of Chemical Technology, 4th ed., vol. 14, 1995, pp. 737-783.

Popoola, A.V. Mechanism of the Reaction Involving the Formation of Dioxane Byproduct During the Production of Poly(ethylene Terephthalate). Applied Plymer Sci.. vol. 43, pp. 1875 and 1877 (1991).

Falbe, J., "New Synthesis with Carbon Monoxide", Springer-Verlang, Berlin Heidelburg, New York, pp. 164-165 (1980).

T. Vermeulen et al., "Adsorption and Ion Exchange", Perry's Chemical Enineer's Handbook, 6th ed., (McGraw-Hill 1984). pp. 16-1 to 16-48.

T. Vermeulen et al., "Adsorption and Ion Exchange", Perry's Chemical Engineer's Handbook, $6^{th}$ ed., (McGraw-Hill 1984). pp. 16-1 to 16-48.

F. Helfferich, "Ion Exchange", Mcgraw Hill, NY (1962), pp. 29-36; 41-57.

K. Dorfner, "Ion Exchangers", Walter de Gruyter, NY, (1991), pp. 31-36.

J. R. Anderson, "Structure of Metallic Catalysts", Academic Press, NY (1975), pp. 34-35.

K. Dorfner, "Ion Exchangers: Properties and Applications", Ann Arbor Science, Ann Arbor, Michigan (1973), pp. 16-26; 69-75.

* cited by examiner

METHOD OF TREATING AN ALDEHYDE MIXTURE, USE OF THE TREATED ALDEHYDE, AND AN ALCOHOL

CROSS-REFERENCE TO RELATED APPLICATIONS

This application claims the benefit of U.S. Provisional Application Nos. 60/763,985, filed Feb. 1, 2006, and 60/820,900, filed Jul. 31, 2006, the disclosures of which are hereby incorporated by reference in their entirety.

FIELD OF INVENTION

This invention relates to a method of treating an aldehyde mixture, use of the treated aldehyde to prepare an alcohol and the alcohol.

BACKGROUND OF THE INVENTION

Aldehydes are commonly prepared and hydrogenated into a corresponding alcohol. A difficulty associated with the process is the oxidation of the aldehyde to form a carboxylic acid by-product. The presence of carboxylic acid, especially if left unneutralized, may have a negative effect on the performance of most heterogeneous hydrogenation catalysts. Additionally, the carboxylic acid may react with the alcohol formed during hydrogenation resulting in additional yield losses and additional separation costs. The carboxylic acid may cause corrosion of processing equipment, especially when present in process streams heated above ambient temperature. Typically, the carboxylic acid is partially neutralized prior to hydrogenation. For example, U.S. 2004/0087819 discloses neutralization of an aqueous 3-hydroxypropionaldehyde solution prior to hydrogenation. However, partial neutralization through the addition of a base, typically an alkali base, is problematic due to the potential degradation of the aldehyde resulting from inefficient mixing. The aldehyde, in the presence of excess base occurring from inefficient mixing, can combine to form byproducts such as acetals and/or aldols which can undergo further condensation to yield polymeric heavy ends. Some of the acids formed are known to be hydroxyacids, where neutralization alone may not fully eliminate the negative impact on the hydrogenation catalyst. Additionally, the resulting alkali metal salt formed during partial neutralization imparts an ash component which substantially reduces the market value of the heavy ends co-product, and the alkali metal salt formed can foul equipment downstream such as the reboilers of downstream distillation columns and heat exchangers.

1,3-propanediol is an industrially important chemical. 1,3-propanediol is used as a monomer unit to form polymers such as poly(trimethylene terphthalate) that are used in the production of carpets and textiles. 1,3-propanediol is also useful as an engine coolant, particularly in cooling systems that require coolants having low conductivity and low corrosivity.

1,3-propanediol may be prepared in a two-step process in which ethylene oxide is first hydroformylated in an organic solution in the presence of a metal catalyst such as a cobalt or rhodium carbonyl to form 3-hydroxypropionaldehyde. The 3-hydroxypropionaldehyde intermediate is water extracted from the organic phase under pressure and the metal catalyst is recycled to the hydroformylation reaction in the organic phase. In a subsequent step, the aqueous 3-hydroxypropionaldehyde is hydrogenated to 1,3-propanediol.

Ideally, the aqueous 3-hydroxypropionaldehyde extract could be routed directly to the hydrogenation reactor. However, as discussed above, the carboxylic acid formed as a byproduct during hydroformylation may have a negative effect on the performance of most heterogeneous hydrogenation catalysts. Additionally, the small amount of metal from the hydroformylation catalyst that typically leaches into the water phase during extraction of 3-hydroxypropionaldehyde also may have a negative effect on the performance of most heterogeneous hydrogenation catalysts.

U.S. 2004/0087819 discloses removing a hydroformylation catalyst from an aqueous 3-hydroxypropionaldehyde solution by utilizing a cation exchange resin. As discussed hereinbefore, the reference also discloses neutralization of the aqueous 3-hydroxypropionaldehyde solution. The neutralization occurs after contact with the cation exchange resin and before hydrogenation.

It goes without saying that it is highly desirable to improve the process for preparing an alcohol from an aldehyde.

SUMMARY OF THE INVENTION

The present invention provides a method of treating an aldehyde mixture comprising a carboxylic acid and a metal cation, which method comprises:

contacting the aldehyde mixture with a basic separating medium, and subsequently or simultaneously contacting with an acidic separating medium. In an embodiment of the invention, the aldehyde comprises 3-hydroxypropionaldehyde, the carboxylic acid comprises 3-hydroxypropionic acid, the metal cation comprises a Group VIII metal cation, and the method additionally comprises controlling the pH of the mixture at a value of at most 6, as measured at a temperature of operation.

The present invention also provides a process for preparing 1,3-propanediol, which process comprises hydrogenating a treated aldehyde mixture which has been obtained by the treatment method in accordance with this invention.

The present invention also provides a 1,3-propanediol product.

DETAILED DESCRIPTION OF THE INVENTION

Figure 1:
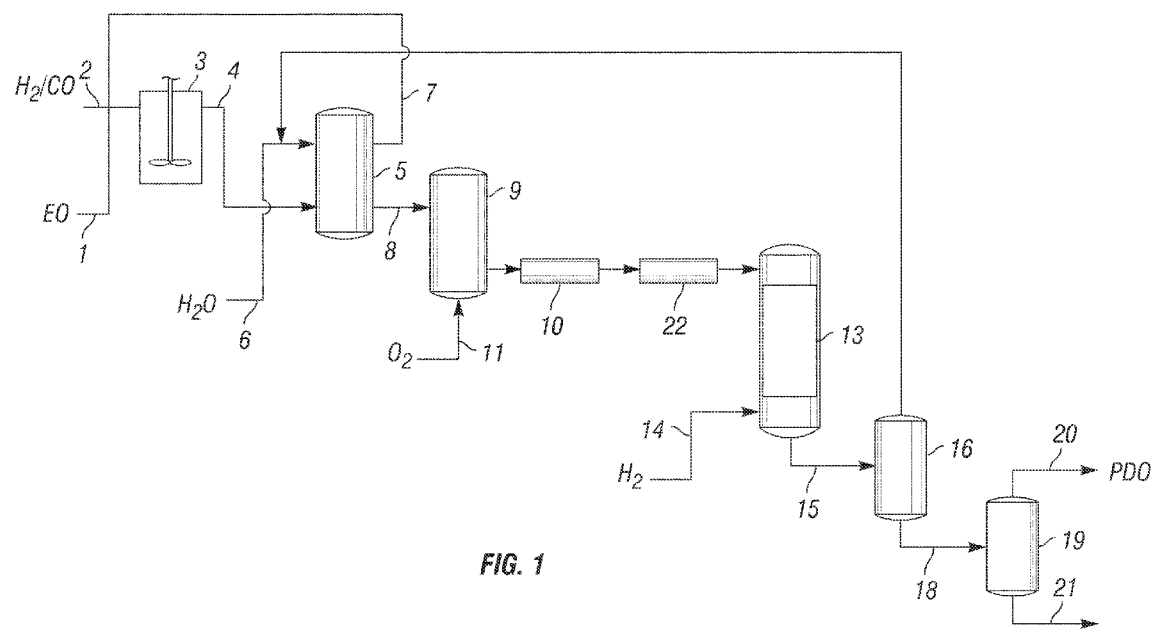
FIG. 1 is a schematic illustrating a process for preparing 1,3-propanediol by hydroformylation of ethylene oxide, carbon monoxide and hydrogen to form 3-hydroxypropionaldehyde followed by hydrogenation of the 3-hydroxypropionaldehyde to 1,3-propanediol which process incorporates the treatment method of the invention.

In accordance with the present invention, processes for producing an alcohol from an aldehyde may be improved by contacting an aldehyde mixture with a basic separating medium and then further contacting with an acidic separating medium. In particular, contacting the aldehyde mixture with a basic separating medium removes at least part of the carboxylic acid present in the mixture such that it may be recovered as a co-product, eliminates the attendant production of an ash component and fouling associated with neutralization of the carboxylic acid, and reduces the subsequent reaction of the carboxylic acid with the alcohol product, as described hereinbefore. Also, contacting the aldehyde mixture with a basic separating medium prior to contacting with an acidic separating medium improves the removal of metal cations present in the mixture.

The aldehyde mixture may be any aldehyde containing mixture. The aldehyde may be any aldehyde and may be a alkyl or aryl aldehyde, hydroxyaldehyde, ketoaldehyde haloaldehyde, or other substituted aldehyde. Preferably, the aldehyde comprises at most 12 carbon atoms, more preferably at most 8 carbon atoms, and most preferably at most 4 carbon atoms. The aldehyde preferably comprises carbon atoms in the range of from 2 to 10, more preferably in the range of from 2 to 4. Preferably the aldehyde comprises 3 carbon atoms, in particular the aldehyde may comprise 3-hydroxypropionaldehyde.

Preferably, the aldehyde mixture may be obtained from the aqueous extraction of a hydroformylation product mix. The term "hydroformylation product mix", as used herein, is a mixture comprising an aldehyde, a hydroformylation catalyst and a carboxylic acid. The hydroformylation product mix may additionally comprise a reaction diluent or "solvent", residual reactants comprising carbon monoxide, hydrogen and an olefin oxide, and minor amounts of other by-products.

The aldehyde mixture may contain the aldehyde in a quantity in the range of from 1 to 99 wt. %, preferably in the range of from 10 to 80 wt. %, more preferably in the range of from 15 to 60 wt. %, and most preferably in the range of from 20 to 40 wt. %, relative to the total weight of the aldehyde mixture.

The carboxylic acid may be any carboxylic acid, preferably comprising at most 12 carbon atoms, more preferably at most 8 carbon atoms, and most preferably at most 4 carbon atoms. The carboxylic acid preferably comprises carbon atoms in the range of from 1 to 10, more preferably in the range of from 1 to 4. The carboxylic acid may comprise one or more carboxylic acids. Preferably, the carboxylic acid comprises the oxidized form of the aldehyde, more preferably, the carboxylic acid comprises a hydroxycarboxylic acid, and most preferably the carboxylic acid comprises 3-hydroxypropionic acid. The carboxylic acid may comprise acetic and formic acid which may be present with 3-hydroxypropionic acid. The aldehyde mixture may contain one or more carboxylic acids in a total quantity in the range of from 0.1 to 5 wt. %; typically in the range of from 0.03 to 3.5 wt. %, more typically in the range of from 0.06 to 1.5 wt. %, and most typically in the range of from 0.1 to 0.8 wt. %, relative to the total weight of the aldehyde mixture.

The metal cation may be any metal cation, preferably the metal cation comprises one or more of a Group IB through Group VIII metal cation (as defined in the Periodic Table of Elements in the "CRC Handbook of Chemistry and Physics", $69^{th}$ ed. (CRC Press Inc. 1988)), more preferably one or more of a Group VIII metal cation, preferably one or more of cobalt, ruthenium, rhodium, palladium, platinum, osmium, and iridium, most preferably rhodium, cobalt, iridium and ruthenium, and in particular cobalt and/or rhodium cations. The metal cation may be contained in one or more metal compounds, complexes or species. The aldehyde mixture may contain the metal cation in a quantity of at most 0.03, typically at most 0.02, more typically at most 0.01, most typically at most 0.002, in particular at most 0.001 molar equivalents of metal cation per liter of aldehyde mixture. The aldehyde mixture may contain the metal cation in a quantity of at least 0.000001, or at least 0.00001, or at least 0.0001 molar equivalents of metal cation per liter of aldehyde mixture.

In an embodiment, the aldehyde mixture may be dissolved in one or more liquid diluents such as water, alcohols, diols, ketones, esters, and glycol ethers. In particular, the diluent comprises water which forms an aqueous solution. The aqueous aldehyde mixture may be any aqueous solution containing an amount of dissolved aldehyde, carboxylic acid and metal cation. Preferably, the aqueous aldehyde mixture may contain from 4 to 60 wt. % aldehyde, and more typically from 20 to 40 wt. % aldehyde, relative to the total weight of the aqueous aldehyde mixture. Preferably, the aqueous aldehyde mixture may contain amounts of carboxylic acid and metal cations as discussed hereinbefore.

The aldehyde mixture may be contacted with a basic separating medium which at least partially separates the carboxylic acid from the aldehyde mixture. The aldehyde mixture resulting from the contacting with the basic separating medium may be referred to as a first aldehyde containing effluent. The basic separating medium may be in any physical form such as a liquid, or preferably a solid.

In an embodiment, the basic separating medium may comprise a basic, anion exchange resin. The ion exchange resins which may be used in the present method may have any physical structure. Preferably, the ion exchange resins used in the present method may have a gel type (microporous) or a macroreticular type (macroporous) structure. The major chemical component of the resin may be based on polyphenol, polystyrene, polyacrylic, or polyvinylpyridine and is typically crosslinked with divinylbenzene. Reference may be made, for example, to Kirk-Othmer's *Encyclopedia of Chemical Technology*, $4^{th}$ Ed., Vol. 14, 1995, pages 737-783.

The basic, anion exchange resin may comprise a weak base anion exchange resin. In particular, the weakly basic, anion exchange resin may have a pKa of less than 13, or a pKb of greater than 1. Weak base anion exchange resins are generally defined as those which cannot split a neutral salt such as NaCl (sodium chloride), unlike strong base anion exchange resins which can. Preferably, the weak base anion exchange resin may be an amine anion exchange resin where the amine is a primary, secondary or tertiary amine, and more preferably a tertiary amine anion exchange resin, and most preferably a dimethylamino styrene divinylbenzene anion exchange resin. Commercially available tertiary amine styrene divinylbenzene anion exchange resins useful in the method of the present invention include AMBERLYST™ A21 tertiary amine styrene divinylbenzene anion exchange resin, available from Rohm & Haas Company, 5000 Richmond Street, Philadelphia, Pa. 19137, USA; and DOWEX™ M-43 tertiary amine styrene divinylbenzene anion exchange resin, available from the Dow Chemical Company, Liquid Separations Group, P.O. Box 1206, Midland, Mich. 48641, USA.

The basic, anion exchange resin may comprise a strong base anion exchange resin. The strong base anion exchange resin may be buffered, preferably a buffered quaternary ammonium anion exchange resin, more preferably a quaternary ammonium anion exchange resin buffered utilizing a mono or dibasic phosphate or carbonate, and most preferably a quaternary ammonium anion exchange resin buffered with dibasic phosphate.

The basic, anion exchange resin may also be incorporated into a mixed resin bed such as Rohm & Haas's STRATABED™ (mixture of weak base anion exchange resin and strong base anion exchange resin), or in a lesser preferred embodiment, a MONOBED™ (strong base anion exchange resin and a strong acid cation exchange resin).

In an alternative embodiment, the basic separating medium may comprise a metal oxide. Preferably, the metal oxide may be one or more of activated alumina, titania, zirconia, chromia and mixtures thereof, and more preferably the metal oxide comprises activated alumina. Without wishing to be bound by theory, it is believed that the metal oxide has basic sites, especially in contact with an aqueous mixture, which can ion exchange acidic species when brought into contact with the metal oxide. Commercially available metal oxides useful in the method of the present invention include Alcoa F200 or LDS aluminas.

The aldehyde mixture may be contacted with the basic separating medium in any manner sufficient to bring the carboxylic acid in the aldehyde mixture into contact with the basic separating medium preferably while minimizing any degradation of the aldehyde. The aldehyde mixture and the basic separating medium may be contacted in a vessel such as a stirred mixing tank, a HIGGINS LOOP™, a carousel-type arrangement, an alternating dual bed-type arrangement, by flow of the mixture through a fixed bed of basic separating medium, or by passing the mixture through a chromatography column containing the basic separating medium. Preferably, the aldehyde mixture and the basic separating medium may be contacted in a HIGGINS LOOP™ or other moving bed arrangements, a carousel-type arrangement, an alternating dual bed-type arrangement, or other fixed-bed arrangements. Reference may be made, for example, to *Perry's Chemical Engineers' Handbook*, $6^{th}$ Ed., 1984, pages 19-40 to 19-45. The HIGGINS LOOP™ is an example of a continuous, countercurrent, exchange column loop system and comprises a closed loop having an ion exchange/adsorption zone, a rinsing zone, a regenerating zone, and a pulsing zone. The carousel-type arrangement may involve the placement of a number of separating medium-containing columns on a carousel, or use of valves to switch feeds in a prescribed manner between a number of fixed columns. When the basic separating medium comprises a metal oxide, the carousel-type arrangement is preferred.

The aldehyde mixture may be contacted with the basic separating medium at a temperature which minimizes the degradation of the aldehyde when in contact with the basic separating medium, preferably at a temperature of from 5 to 45° C., and more preferably at a temperature of from 15 to 25° C.

Preferably, the aldehyde mixture may be contacted with the basic separating medium while controlling the pH of the aldehyde mixture at a value of at most 6, more preferably at most 5.5, and most preferably at most 5. By controlling the pH of the aldehyde mixture, any degradation of the aldehyde may be minimized. Preferably, only 90 to 98% of the original carboxylic acid is removed by the basic separating medium, leaving 2 to 10% of the original acid to maintain pH in the range described hereinbefore. Depending on the initial acid concentration, this may correspond to a concentration of unneutralized acid of between about $1 \times 10^{-6}$ and $2 \times 10^{-3}$ molar equivalents of carboxylic acid per liter of aldehyde mixture. The desired amount of residual carboxylic acid may be readily achieved via a control system based upon direct monitoring of pH.

Unless otherwise stated, the pH values are deemed to be directly measured at the temperature of operation, using a conventional standard pH probe immersed in the aldehyde mixture.

The amount of the carboxylic acid removed from the aldehyde mixture and the resulting pH may be dependent on several factors. In particular, the amount of acid removal and pH may be dependent on the separating capacity of the basic separating medium, the amount of basic separating medium employed in the separation step relative to the amount of aldehyde mixture present for contact with the basic separating medium, the amount of carboxylic acid present in the aldehyde mixture, the apparatus used to effect contact between the aldehyde mixture and the basic separating medium, and the contact time for the process. These factors, in particular the time duration of the contacting step, may be adjusted to control the acid removal and the pH of the aldehyde mixture.

For a batch-type process, a sufficient amount of basic separating medium by weight of medium to weight of aldehyde mixture may be from 0.1 to 25 weight percent and preferably from 1 to 10 weight percent, relative to the weight of the aldehyde mixture. For a continuous process, the aldehyde mixture may be passed through the basic separating medium at a volume hourly space velocity (volume of aldehyde mixture feed per volume of basic separating medium per hour) of from $0.1\ h^{-1}$ to $40\ h^{-1}$, preferably from $0.5\ h^{-1}$ to $20\ h^{-1}$, and more preferably from $1\ h^{-1}$ to $10\ h^{-1}$.

Preferably, the contact between the aldehyde mixture which has had the carboxylic acid removed to pH values as discussed hereinbefore and unneutralized basic separating medium is avoided. This may be accomplished by adjusting the factors, as discussed hereinbefore, preferably by additionally using continuous ion exchange, in particular short beds with high dispersive mixing, or backmixed stages with frequent regeneration. It is preferred to apply continuous ion exchange where the total ion exchange bed volume is broken up into a series of "N" equivalent stages either by use of discrete vessels (carousel-type) or via periodically pulsing the bed through the ion exchange zone (HIGGINS™ LOOP). The volume hourly space velocity for a single stage is thus "N"-times higher than for a single larger bed. The higher volume hourly space velocity results in mixing within stage due to axial dispersion so that high pH regions in the bed, due to locally complete acid removal, are avoided. As a result, degradation of the aldehyde is minimized and the method operates with a more constant and optimal outlet pH than with a larger bed.

The first aldehyde containing effluent may contain at least 70 percent of the aldehyde present in the aldehyde mixture, more preferably at least 80 percent, and most preferably at least 90 percent.

The first aldehyde containing effluent may contain a smaller quantity of the carboxylic acid than the aldehyde mixture, and preferably the first aldehyde containing effluent may contain at most 20 percent of the carboxylic acid present in the aldehyde mixture, more preferably at most 10 percent, and most preferably at most 5 percent. The first aldehyde containing effluent may contain at least 1 percent of the carboxylic acid present in the aldehyde mixture, more preferably at least 1.5 percent, and most preferably at least 2 percent. The pH of the first aldehyde containing effluent may be at most 6, preferably at most 5.5, and more preferably at most 5.

The amount of metal cations in the first aldehyde containing effluent may be the same as the amount of metal cations in the aldehyde mixture since the metal cations may not be removed in any significant quantity by the basic separating medium.

After the separating capacity has diminished, the basic separating medium may be subjected to a base treatment to regenerate the basic properties of the separating medium. Preferably, the base treatment may be a base wash if the basic separating medium is a solid. Prior to the base wash, the basic separating medium may be subjected to a water wash. The basic separating medium may be contacted with the base wash for a sufficient time and in a sufficient concentration to regenerate the basic properties of the separating medium. The base wash may have a pH above that of the $pK_b$ of the basic separating medium to most fully regenerate the medium. The base wash will preferably have a pH of 8 or above, more preferably a pH of 10 or above. The base wash is preferably a potassium hydroxide solution, more preferably a 4 wt. % potassium hydroxide solution. Other bases, however, may be utilized as the base wash, including, but not limited to, sodium hydroxide, ammonium hydroxide, or other metal hydroxides. The basic separating medium may be contacted with the base wash at a temperature of from 5 to 45° C.

The first aldehyde containing effluent may be subsequently or simultaneously contacted with an acidic separating medium to yield a treated aldehyde mixture. The treated aldehyde mixture resulting from the contacting with the acidic separating medium may be referred to as a second aldehyde containing effluent. Contacting the first aldehyde containing effluent with the acidic separating medium at least partially separates the metal cations from the first aldehyde containing effluent.

Preferably, the first aldehyde containing effluent may be separated from the basic separating medium and subsequently contacted with the acidic separating medium. The first aldehyde containing effluent may or may not have undergone further modification before contacting the acidic separating medium whereby the concentration of components in the effluent is changed. The modification of the effluent may include any process such as dilution or concentration. Preferably, the process does not substantially change the chemical structure of the aldehyde. A substantial change is understood to mean typically there is no more than a 25 percent decrease in the molar quantity of aldehyde present in the effluent. The acidic separating medium may be in any physical form such as a liquid or preferably a solid.

The acidic separating medium may comprise a carboxylic acid cation exchange resin, i.e., a weak acid cation exchange resin. Preferably, the carboxylic acid cation exchange resin may be an acrylic acid cation exchange resin. The carboxylic acid cation exchange resins which may be used in the present method may have any physical structure, preferably, a gel type (microporous) or a macroreticular type (macroporous) structure. Commercially available acrylic acid cation exchange resins include DOW MAC-3 acrylic acid cation exchange resin, available from The Dow Chemical Company, Liquid Separations, P.O. Box 1206, Midland, Mich. 48642, USA; IRC76 acrylic acid cation exchange resin, available from Rohm & Haas Company, Ion Exchange Resins, 100 Independence Mall West, Philadelphia, Pa. 19106, USA; and C140E acrylic acid cation exchange resin, available from The Purolite Company, 150 Monument Road, Bala Cynwyd, Pa. 19004, USA.

The first aldehyde containing effluent may be contacted with the acidic separating medium in any manner sufficient to ensure that the metal cations in the first aldehyde containing effluent are brought into contact with the acidic separating medium. For example, the first aldehyde containing effluent and the acidic separating medium may be contacted in a vessel such as a stirred mixing tank, a HIGGINS LOOP™, a carousel-type arrangement, an alternating dual bed-type arrangement, by flow of the mixture through a fixed bed of separating medium, or by passing the mixture through a chromatography column containing the acidic separating medium.

For a batch-type process, a sufficient amount of acidic separating medium by weight of medium to weight of first aldehyde containing effluent may be in the range of from 1:5 to 1:25, and preferably in the range of from 1:10 to 1:15. Contact times may vary from 30 minutes to several hours, for example from 1 to 50 hours. For a continuous process, the first aldehyde containing effluent may be passed through the acidic separating medium at a volume hourly space velocity (volume of first aldehyde containing effluent feed per volume of acidic separating medium per hour) of from $0.1\ h^{-1}$ to $100\ h^{-1}$, preferably from $2\ h^{-1}$ to $30\ h^{-1}$.

The first aldehyde containing effluent may be contacted with the acidic separating medium at any temperature that minimizes degradation of the separating medium or the aldehyde. Preferably, the first aldehyde containing effluent and the acidic separating medium may be contacted at a temperature of from 5 to 45° C., and more preferably of from 15 to 25° C.

The second aldehyde containing effluent may contain at least 70 percent of the aldehyde present in the aldehyde mixture, more preferably at least 80 percent, and most preferably at least 90 percent.

The second aldehyde containing effluent may contain at least 70 percent of the aldehyde present in the first aldehyde containing effluent, more preferably at least 80 percent, and most preferably at least 90 percent. The second aldehyde containing effluent may contain a smaller quantity of the metal cations than the aldehyde mixture and first aldehyde containing effluent, and preferably the second aldehyde containing effluent may contain at most 50 percent, more preferably at most 25 percent, and most preferably at most 10 percent of the metal cations present in the aldehyde mixture and first aldehyde containing effluent. Preferably, the second aldehyde containing effluent may contain a total of at most 0.001, more preferably at most 0.0001, and most preferably at most 0.00001 molar equivalents of the metal cations per liter of the second aldehyde containing effluent.

The second aldehyde containing effluent may or may not have undergone further modification prior to hydrogenation whereby the concentration of components in the effluent is changed. The modification of the effluent may include any process such as dilution or concentration.

After the separating capacity has diminished, the acidic separating medium may be subjected to an acid treatment to regenerate the acidic properties of the separating medium. Preferably, the acid treatment may be an acid wash if the acidic separating medium is a solid. The acidic separating medium may be contacted with an acid wash at a temperature of at least 45° C., preferably in the range of from 70 to 100° C., most preferably from 85 to 95° C., for a sufficient time to regenerate the acidic properties of the acidic separating medium. The acid wash should have a pH below that of the $pK_a$ of the acidic separating medium to most fully regenerate the separating medium. Unless otherwise stated, the $pK_a$ values are deemed to be measured at a temperature of 25° C. The acid wash will preferably have a pH of 2 or below, more preferably a pH of 1 or below. The acid wash is preferably a sulfuric acid solution, more preferably a 10% sulfuric acid solution. Other acids, however, may be utilized as the acid wash, including, but not limited to, hydrochloric acid, phosphoric acid, or other mineral acids.

Referring now to FIG. 1, FIG. 1 is a schematic illustrating a process for preparing 1,3-propanediol by hydroformylation of ethylene oxide, carbon monoxide and hydrogen to form 3-hydroxypropionaldehyde followed by hydrogenation of the 3-hydroxypropionaldehyde to 1,3-propanediol which process incorporates the treatment method of the invention.

FIG. 1 depicts an embodiment of the invention within the 1,3-propanediol process. Separate or combined streams of ethylene oxide (1), carbon monoxide and hydrogen (2) are charged to hydroformylation vessel (3) and reacted in the presence of a hydroformylation catalyst to produce a hydroformylation product mix.

Following the hydroformylation reaction, the hydroformylation product mix containing 3-hydroxypropionaldehyde may be cooled and passed to extraction vessel (5) via line (4), where an aqueous liquid, generally water and optional miscibilizing diluent, are added via line (6) for extraction and concentration of the 3-hydroxypropionaldehyde for the subsequent hydrogenation step. The organic phase resulting from the liquid-liquid extraction may be recycled, with optional purge of heavy ends, from the extraction vessel to hydroformylation reaction via line (7). The aqueous 3-hydroxypropionaldehyde solution generated from the liquid-liquid extraction may be passed via line (8) to degasser-stripper-oxidizer vessel (9) for removal of carbon monoxide and hydrogen and for oxidation of any remaining catalyst in carbonyl form. Oxidation may be conveniently carried out by introducing an oxygen-containing gas such as air into the aqueous 3-hydroxypropionaldehyde solution extract. The preferred oxidation technique involves sparging air from inlet (11) in an upward direction through degasser-stripper-oxidizer vessel (9) as the aqueous 3-hydroxypropionaldehyde solution to be treated flows in a downward direction through vessel (9). The stripping gas may be sparged through the degasser-stripper-oxidizer vessel (9) through the same inlet (11) as the oxidizing gas, or through a separate inlet (not shown) positioned to permit the stripping gas to flow through the aqueous 3-hydroxypropionaldehyde solution as the solution flows through vessel (9).

In the method of the present invention, the aqueous 3-hydroxypropionaldehyde solution, i.e., the aqueous 3-hydroxypropionaldehyde mixture, may be passed from vessel (9) to vessel (10) where carboxylic acid may be separated by contacting the aqueous 3-hydroxypropionaldehyde mixture with the basic separating medium. The first 3-hydroxypropionaldehyde containing effluent resulting from vessel (10) may then be passed to vessel (22) where the metal cations may be separated by contacting the first 3-hydroxypropionaldehyde containing effluent with an acidic separating medium.

The second 3-hydroxypropionaldehyde containing effluent resulting from vessel (22) may then be passed to the hydrogenation zone (13) and reacted with hydrogen (14) in the presence of a hydrogenation catalyst to produce a hydrogenation product mixture (15) containing 1,3-propanediol. In such a process, the illustrated hydrogenation zone (13) includes a series of two or more separate reaction vessels.

Residual diluent and extractant water may be recovered by distillation of the hydrogenation product mixture (15) in column (16) and recycled to a water extraction process for further distillation (not shown) and separation and purge of light ends. 1,3-propanediol containing product stream (18) may be passed to a distillation column (19) for recovery of 1,3-propanediol (20) from heavy ends (21).

The hydroformylation vessel may be a pressure reaction vessel such as a bubble column or agitated tank, operated batchwise or in a continuous manner. The feed streams may be contacted in the presence of a hydroformylation catalyst. The hydroformylation catalyst may comprise one or more metal cations, as described hereinbefore. The hydroformylation catalyst may further comprise a carbonyl, in particular water-insoluble cobalt and/or rhodium carbonyls such as $CO_4(CO)_{12}$ (tetracobalt dodecacarbonyl), $Co_2(CO)_8$ (dicobalt octacarbonyl) and $Rh_6(CO)_{16}$ (hexarhodium hexadecacarbonyl). The hydroformylation catalyst will typically be present in the reaction mixture in an amount within the range of 0.01 to 1 wt. %, preferably from 0.05 to 0.3 wt. %, relative to the total weight of the hydroformylation reaction mix. The hydrogen and carbon monoxide will generally be introduced into the reaction vessel in a molar ratio within the range of 1:2 to 8:1, preferably 1:1 to 6:1.

The hydroformylation reaction may be carried out under conditions effective to produce a hydroformylation product mix containing a major portion of 3-hydroxypropionaldehyde and a minor portion of acetaldehyde and 1,3-propanediol. The level of 3-hydroxypropionaldehyde in the reaction mixture is preferably less than 15 wt. %, more preferably within the range of 5 to 10 wt. %, relative to the total weight of the hydroformylation reaction mixture. To provide for diluents having different densities, the desired concentration of 3-hydroxypropionaldehyde in the reaction mixture can be expressed in molarity, i.e., less than 1.5M, preferably within the range of 0.5M to 1M. Generally, the cobalt-catalyzed hydroformylation reaction may be carried out at a temperature of less than 100° C., preferably 60° C. to 90° C., and most preferably 75° C. to 85° C., with rhodium-catalyzed hydroformylations on the order of about 10° C. higher. The hydroformylation reaction may generally be carried out at a pressure within the range of 1 to 35 MPa, preferably (for process economics) 7 to 25 MPa, with higher pressures preferred for greater selectivity. The hydroformylation reaction may be carried out in a liquid diluent inert to the reactants. By "inert" is meant that the diluent is not consumed during the course of the reaction. In general, ideal diluents for the hydroformylation process will solubilize carbon monoxide, will be essentially non-water miscible, and will dissolve 3-hydroxypropionaldehyde to the desired concentration of at least 5 wt. % under hydroformylation conditions, while most of the diluent will remain as a separate phase upon water extraction. By "essentially non-water miscible" is meant that the diluent has a solubility in water at 25° C. of less than 25 wt. %, so as to form a separate organic phase upon water-extraction of 3-hydroxypropionaldehyde from the hydroformylation product mix. Preferably, the hydroformylation reaction diluents may be alcohols and ethers. More preferably, the hydroformylation reaction diluents may be ethers such as methyl-t-butyl ether, ethyl-t-butyl ether, diethyl ether, phenylisobutyl ether, ethoxyethyl ether, diphenyl ether, and diisopropyl ether. Blends of diluents such as tetrahydrofuran/toluene, tetrahydrofuran/heptane, and t-butylalcohol/hexane may also be used. Most preferably, the hydroformylation reaction diluent may be methyl-t-butyl ether because of the high yields of 3-hydroxypropionaldehyde which can be achieved under moderate reaction conditions.

To further enhance yields under moderate reaction conditions, the hydroformylation reaction mix will preferably include a catalyst promoter to accelerate the reaction rate. Preferred lipophilic promoters include lipophilic phosphonium salts and lipophilic amines, which accelerate the rate of hydroformylation without imparting hydrophilicity (water solubility) to the active catalyst. Preferably, the lipophilic promoters may be tetrabutylphosphonium and dimethyldodecyl amine. As used herein, "lipophilic" means that the promoter tends to remain in the organic phase after extraction of 3-hydroxypropionaldehyde with water. The promoter will generally be present in an amount within the range of 0.01 to 1 mole per mole of metal component of the catalyst (e.g. cobalt and/or rhodium).

At low concentrations, water serves as a promoter for the formation of the desired carbonyl catalyst species. Optimum water levels for hydroformylation in methyl-t-butyl ether diluent are within the range of 1 to 2.5 wt. %, relative to the total weight of the hydroformylation reaction mix. An excessive amount of water, however, reduces 3-hydroxypropionaldehyde selectivity and may induce formation of a second liquid phase.

Liquid-liquid extraction of the 3-hydroxypropion-aldehyde into the water can be effected by any suitable means, such as mixer-settlers, packed or trayed extraction columns, or rotating disk contactors. The amount of water added to the hydroformylation product mix will generally be within the range of 1:1 to 1:20, preferably 1:5 to 1:15 by volume. Water extraction may preferably be carried out at a temperature within the range of 25° C. to 55° C., with a lower temperature preferred. Water extraction under a partial pressure for carbon monoxide of 0.5-5 MPa at 25° C. to 55° C. maximizes catalyst retention in the organic phase.

Typically, the organic phase resulting from the liquid-liquid extraction contains a major portion of the hydroformylation reaction diluent and a major portion of the catalyst. The organic phase may be recycled, with optional purge of heavy ends, from the extraction vessel to hydroformylation reaction.

Preferably, the aqueous 3-hydroxypropionaldehyde mixture generated from the liquid-liquid water extraction may contain from 4 to 60 wt. % 3-hydroxypropionaldehyde, more preferably from 20 to 40 wt. % 3-hydroxypropionaldehyde, relative to the total weight of the aqueous 3-hydroxypropionaldehyde mixture.

The aqueous 3-hydroxypropionaldehyde mixture may have a pH in the range of from 2 to 4, typically from 2.5 to 3.5, and more typically from 2.9 to 3.3.

The aqueous 3-hydroxypropionaldehyde mixture may contain a quantity of carboxylic acid in the range of from 0.03 to 3 wt. %; typically in the range of from 0.06 to 1 wt. %; and more typically in the range of from 0.1 to 0.6 wt. %, relative to the total weight of the aqueous 3-hydroxypropionaldehyde mixture.

Typically, the carboxylic acid comprises 3-hydroxypropionic acid in a quantity of at least 50 wt. %, more typically at least 60 wt. %, most typically at least 75 wt. %, in particular at least 90 wt. %, relative to the total weight of the carboxylic acid present in the aqueous 3-hydroxypropionaldehyde mixture.

The aqueous 3-hydroxypropionaldehyde mixture may contain a total quantity of cobalt and/or rhodium cations of at most 0.03, typically at most 0.02, more typically at most 0.01, most typically at most 0.002, in particular at most 0.001 molar equivalents of cobalt and/or rhodium cations per liter of the aqueous 3-hydroxypropionaldehyde mixture. The aqueous 3-hydroxypropionaldehyde mixture may contain a total quantity of cobalt and/or rhodium cations of at least 0.000001, or at least 0.00001, or at least 0.0001 molar equivalents of cobalt and/or rhodium cations per liter of the aqueous 3-hydroxypropionaldehyde mixture. Typically, the aqueous 3-hydroxypropionaldehyde mixture may contain a total quantity of cobalt and/or rhodium cations in the range of from 0.001 to 0.003 molar equivalents of cobalt and/or rhodium cations per liter of the aqueous 3-hydroxypropionaldehyde mixture. The quantity of cobalt and/or rhodium cations includes cobalt and/or rhodium cations from both water soluble and water-insoluble complexes, compounds or species.

The aqueous 3-hydroxypropionaldehyde solution generated from the liquid-liquid water extraction may be oxidized. Preferably, the aqueous 3-hydroxypropionaldehyde mixture may be contacted with oxygen under weakly acidic conditions effective for oxidation of insoluble metal compounds, e.g. water insoluble cobalt and/or rhodium species, to water soluble metal compounds, e.g. water soluble cobalt and/or rhodium cations. The oxidation of insoluble metal compounds facilitates removal of the metal compounds in the subsequent ion exchange step.

Typically, the quantity of carboxylic acid produced as a byproduct of ethylene oxide hydroformylation under conditions favoring the formation of 3-hydroxypropionaldehyde generates weakly acidic conditions suitable for oxidation. If sufficient acid is not already present as a reaction byproduct, the aqueous 3-hydroxypropionaldehyde solution may be made acidic by addition of an organic or inorganic acid in an amount effective to produce a solution having a pH from 3 to 6, preferably from 3 to 4. Suitable acids include $C_{1-4}$ organic acids.

The oxidation may be carried out at a temperature of from 5° C. to 45° C. and at a pressure in the range of from 50 to 200 kPa, preferably about 101.3 kPa (atmospheric pressure). The residence time may typically be in the range of from 1 to 15 minutes.

A stripping gas such as nitrogen or carbon dioxide may also be sparged through the aqueous 3-hydroxypropionaldehyde solution in the degasser-stripper-oxidizer to prevent formation of flammable mixtures and to assist in removal of carbon monoxide and hydrogen from the aqueous 3-hydroxypropionaldehyde solution. It is desirable to remove even minor amounts of carbon monoxide remaining in the solution since carbon monoxide can interfere with the performance of the hydrogenation catalyst.

After passing through the degasser-stripper-oxidizer, the resulting aqueous 3-hydroxypropionaldehyde mixture may contain 3-hydroxypropionaldehyde and byproducts including, one or more water soluble metal cations and carboxylic acid, the major component being 3-hydroxypropionic acid.

The aqueous 3-hydroxypropionaldehyde mixture obtained from the degasser-stripper-oxidizer may be contacted with a basic separating medium yielding a first 3-hydroxypropionaldehyde containing effluent. As discussed hereinbefore, the basic separating medium may be contacted with the aqueous 3-hydroxypropionaldehyde mixture while controlling the pH of the mixture at a value of at most 6, preferably at most 5.5, and more preferably at most 5, in order to minimize the degradation of the 3-hydroxypropionaldehyde. 3-hydroxypropionaldehyde may be increasingly degraded above pH 5 and may be significantly degraded at pH values above 6.

The conditions and vessels for contacting the aqueous 3-hydroxypropionaldehyde mixture with the basic separating medium may be as discussed hereinbefore for the aldehyde mixture.

The first 3-hydroxypropionaldehyde containing effluent may contain at least 70 percent of the aldehyde present in the aqueous 3-hydroxypropionaldehyde mixture, more preferably at least 80 percent, and most preferably at least 90 percent.

The first 3-hydroxypropionaldehyde containing effluent may contain a smaller quantity of the carboxylic acid than the aqueous 3-hydroxypropionaldehyde mixture, and preferably the first 3-hydroxypropionaldehyde containing effluent may contain at most 20 percent of the carboxylic acid present in the aqueous 3-hydroxypropionaldehyde mixture, more preferably at most 10 percent, and most preferably at most 5 percent. The first 3-hydroxypropionaldehyde containing effluent may contain at least 1 percent of the carboxylic acid present in the aqueous 3-hydroxypropionaldehyde mixture, more preferably at least 1.5 percent, and most preferably at least 2 percent. The pH of the first 3-hydroxypropionaldehyde containing effluent may be at most 6, preferably at most 5.5, and more preferably at most 5.

The amount of metal cations in the first 3-hydroxypropionaldehyde containing effluent may be the same as the amount of metal cations in the aqueous 3-hydroxypropionaldehyde mixture since the metal cations are not removed in any significant quantity by the basic separating medium.

The first 3-hydroxypropionaldehyde containing effluent may be contacted with an acidic separating medium yielding a second 3-hydroxypropionaldehyde containing effluent. The conditions and vessels for contacting the first 3-hydroxypropionaldehyde containing effluent with the acidic separating medium may be as discussed hereinbefore for the first aldehyde containing effluent.

The second 3-hydroxypropionaldehyde containing effluent may contain at least 70 percent of the aldehyde present in the aqueous 3-hydroxypropionaldehyde mixture, more preferably at least 80 percent, and most preferably at least 90 percent.

The second 3-hydroxypropionaldehyde containing effluent may contain at least 70 percent of the aldehyde present in the first 3-hydroxypropionaldehyde containing effluent, more preferably at least 80 percent, and most preferably at least 90 percent.

The second 3-hydroxypropionaldehyde containing effluent may contain a smaller quantity of the metal cations than the aqueous 3-hydroxypropionaldehyde mixture or first 3-hydroxypropionaldehyde containing effluent, and preferably the second 3-hydroxypropionaldehyde containing effluent may contain at most 50 percent, more preferably at most 25 percent, and most preferably at most 10 percent of the metal cations present in the aqueous 3-hydroxypropionaldehyde mixture or first 3-hydroxypropionaldehyde containing effluent. Preferably, the second 3-hydroxypropionaldehyde containing effluent may contain a total of at most 0.001, more preferably at most 0.0001, and most preferably at most 0.0001 molar equivalents of the metal cations per liter of the second 3-hydroxypropionaldehyde containing effluent.

The pH of the second 3-hydroxypropionaldehyde containing effluent may be in the range of from 3 to 6, preferably in the range of from 3.5 to 5.5.

The hydrogenation catalyst may preferably be a fixed-bed supported nickel catalyst, such as is available commercially as Calsicat E-475SRand R-3142 from W.R. Grace.

The hydrogenation process may be carried out in one stage or two or more sequential temperature stages. In a preferred embodiment, hydrogenation may be carried out as described above at a temperature within the range of 50° C. to 130° C., followed by a second stage carried out at a temperature higher than that of the first stage and within the range of 70° C. to 155° C., and then optionally a third stage at a temperature greater than 120° C. for reversion of heavy ends to 1,3-propanediol.

Having generally described the invention, a further understanding may be obtained by reference to the following examples, which are provided for purposes of illustration only and are not to be construed as limiting the scope of the invention described herein.

EXAMPLE 1

Preparation of an aqueous 3-hydroxypropionaldehyde mixture for use in Examples 2-4:

An ethylene oxide hydroformylation product mix was water extracted under 1350 psi (9300 kPa) of 4:1 hydrogen: carbon monoxide at 35° C., the aqueous extract layer forming an aqueous solution. After depressuring to atmospheric pressure, the aqueous extract layer was separated and sparged with a dilute air/nitrogen mixture to convert the cobalt carbonyl catalyst to a water-soluble cationic cobalt metal species. The aqueous 3-hydroxypropionaldehyde mixture was analyzed by gas chromatography to determine a 3-hydroxypropionaldehyde concentration of 12.25 wt. % for the aqueous 3-hydroxypropionaldehyde mixture. A calorimetric technique based on derivitization of thiocyanate was used to determine a cobalt concentration of 77 ppmw. Titration of acidity with a 0.1N KOH titrant resulted in a concentration of 0.051 meq of carboxylic acid per gram of 3-hydroxypropionaldehyde mixture at an equivalence point between pH=8 and 9 when measured at a temperature of 25° C. The pH of the aqueous 3-hydroxypropionaldehyde mixture was 3.3, when measured at a temperature of 25° C. The aqueous 3-hydroxypropionaldehyde mixture was divided into a number of aliquots used in examples 2-4.

EXAMPLE 2

In accordance with the method of the invention, the effectiveness of a basic separating medium, in particular a tertiary amine ion exchange resin, to remove carboxylic acid from an aqueous 3-hydroxypropionaldehyde mixture and the effectiveness of an acidic separating medium, in particular a carboxylic acid cation exchange resin, to remove cobalt cations from a first 3-hydroxypropionaldehyde containing effluent was determined. 10 grams of the aqueous 3-hydroxypropionaldehyde mixture from example 1 were contacted with 1 wet grams of AMBERLYST™ A-21 (a dimethylamino macroreticular styrene divinylbenzene available from Rohm and Haas Company) ion exchange resin, via tumbling for 18 hours at 24° C. in a glass vial to insure liquid-solid equilibration. A separate sample of the resin was dried via vacuum oven overnight at 65° C. to establish a dry solids content of 52 wt. % of the wet resin. Analysis of the liquid phase after contact with the resin (i.e., the first 3-hydroxypropionaldehye containing effluent) revealed a pH of 5, as measured at 25° C., a carboxylic acid concentration of 0.002 meq/g, a cobalt concentration of 76 ppmw, and a 3-hydroxypropionaldehyde concentration of 11.9 wt. %. Any difference of less than 3 wt. % between the initial and final concentration of 3-hydroxypropionaldehyde is negligible given normal experimental error in gas chromatography analysis of this reactive intermediate.

This demonstrates that a basic separating medium may be used to remove 96% by weight of the carboxylic acid present in the aqueous 3-hydroxypropionaldehyde mixture with negligible degradation of the 3-hydroxypropionaldehyde.

4.55 grams of residual liquid supernatant (i.e., the first 3-hydroxypropionaldehyde containing effluent) was contacted with 0.038 wet grams of DOWEX™ Mac-3 (a macroreticular acrylic acid available from The Dow Chemical Company) ion exchange resin, via tumbling for 18 hours at 24° C. in a glass vial. A separate sample of the resin was dried via vacuum oven overnight at 65° C. to establish a dry solids content of 53 wt. % of the wet resin. Analysis of the liquid phase after contact with the resin (i.e., the second 3-hydroxypropionaldehyde containing effluent) revealed a pH of 4.4, a cobalt concentration of 18 ppmw, and a 3-hydroxypropionaldehyde concentration of 11.5 wt. %.

The combined contact with a basic separating medium and an acidic separating medium removed 96% by weight of the carboxylic acid and 77% by weight of the cobalt with only a 7% by weight degradation of the 3-hydroxypropionaldehyde, relative to the aqueous 3-hydroxypropionaldehyde mixture. The ratio of the concentration of cobalt on the resin (based on dry gram) per concentration of cobalt remaining in the second 3-hydroxypropionaldehyde containing effluent was 741.

EXAMPLE 3 (COMPARATIVE)

4.34 grams of the first 3-hydroxypropionaldehyde containing effluent from example 2 was contacted with an additional 0.56 wet grams of AMBERLYST™ A-21 (a dimethylamino macroreticular styrene divinylbenzene available from Rohm and Haas Company) ion exchange resin, via tumbling for 18 hours at 24° C. in a glass vial. Analysis of the liquid phase after continued contact with the resin revealed complete removal of the carboxylic acid, a pH of 7.07, a cobalt concentration of 76 ppmw, and a 3-hydroxypropionaldehyde concentration of 3.17 wt. %.

This example demonstrates that not controlling the pH of the aqueous 3-hydroxypropionaldehyde mixture results in degradation of 3-hydroxypropionaldehyde once the carboxylic acid has been removed from the aqueous 3-hydroxypropionaldehyde mixture.

EXAMPLE 4 (COMPARATIVE)

A 10 gram aliquot of the aqueous 3-hydroxypropionaldehyde mixture from example 1 was contacted with 0.063 dry grams of DOWEX™ Mac-3 (a macroreticular acrylic acid available from The Dow Chemical Company) ion exchange resin, via tumbling for 18 hours at 24° C. in a glass vial. Analysis of the liquid phase after contact with the resin revealed a pH of 3.3, a cobalt concentration of 48 ppmw, and a 3-hydroxypropionaldehyde concentration of 12.45 wt. %. The ratio of the concentration of cobalt on the resin (based on dry gram) per concentration of cobalt remaining in the aqueous mixture of 3-hydroxypropionaldehyde was 96.

Comparison of Example 2 with Example 4 demonstrates that treatment with a basic separating medium before contact with an acidic separating medium substantially improves the amount of cobalt removed by the acidic separating medium while minimizing the degradation of the 3-hydroxypropionaldehyde.

EXAMPLE 5

The effectiveness of metal oxide to remove carboxylic acid from an aqueous 3-hydroxypropionaldehyde mixture in accordance with the method of the invention is determined.

An aqueous 3-hydroxypropionaldehyde mixture was prepared similar to Example 1 except the aqueous 3-hydroxypropionaldehyde mixture had a concentration of 3-hydroxypropionaldehyde of 22 wt. %, and a concentration of carboxylic acid of 0.041 meq/g of solution.

2 grams of LDS, an activated alumina available from Coastal Chemical Corporation, was water washed to remove residual base and air dried. The water washed LDS was added to a vial containing 18 grams of the aqueous 3-hydroxypropionaldehyde mixture obtained from an ethylene oxide hydroformylation product mix. The vial was rotated on a rack for 68 hours at room temperature. The LDS alumina removed 79% by weight of the acid which resulted in a pH of 3.3 for the first 3-hydroxypropionaldehyde containing effluent and less than 4 wt. % of the 3-hydroxypropionaldehyde was degraded after contact with the LDS alumina.

This demonstrates that a metal oxide may be used to remove carboxylic acid present in the aqueous 3-hydroxypropionaldehyde mixture with minimal degradation of the 3-hydroxypropionaldehyde.

The first 3-hydroxypropionaldehyde containing effluent is then contacted with a quantity of DOWEX™ Mac-3 (a macroreticular acrylic acid available from The Dow Chemical Company) ion exchange resin to yield a second 3-hydroxypropionaldehyde containing effluent. The second 3-hydroxypropionaldehyde containing effluent will contain a lesser quantity of cobalt than present in the first 3-hydroxypropionaldehyde containing effluent.

EXAMPLE 6

The effectiveness of metal oxide in a continuous process to remove carboxylic acid from an aqueous 3-hydroxypropionaldehyde mixture in accordance with the method of the invention is determined.

1300 grams of LDS alumina were packed into a 2-inch (5 cm) by 18-inch (46 cm) column. Aqueous 3-hydroxypropionaldehyde mixture was fed to the column at a weight hourly space velocity (WHSV hr$^{-1}$) of between 0.4 and 0.6 hr$^{-1}$. The aqueous 3-hydroxypropionaldehyde mixture contained a carboxylic acid concentration in the range of from 0.021 to 0.038 meq/g of solution and a quantity of 3-hydroxypropionaldehyde of 17 to 23 wt. %. The first 3-hydroxypropionaldehyde containing effluent showed negligible degradation of 3-hydroxypropionaldehyde after contact with the alumina while still removing 92% by weight of the acid present in the aqueous 3-hydroxypropionaldehyde mixture. After breakthrough of the acid, regeneration of the alumina was performed using 4 wt. % potassium hydroxide solution.

The first 3-hydroxypropionaldehyde containing effluent is then contacted with a quantity of DOWEX™ Mac-3 (a macroreticular acrylic acid available from The Dow Chemical Company) ion exchange resin to yield a second 3-hydroxypropionaldehyde containing effluent. The second 3-hydroxypropionaldehyde containing effluent will contain a lesser quantity of cobalt than present in the first 3-hydroxypropionaldehyde containing effluent.

We claim:

1. A method of treating an aldehyde mixture comprising a carboxylic acid and a metal cation, which method comprises:
   contacting the aldehyde mixture with a basic separating medium, and
   subsequently or simultaneously contacting with an acidic separating medium.

2. The method as claimed in claim 1, wherein the method additionally comprises controlling the pH of the aldehyde mixture at a value of at most 6, as measured at a temperature of operation.

3. The method as claimed in claim 2, wherein the pH of the aldehyde mixture is maintained at a pH of at most 5, as measured at a temperature of operation.

4. The method as claimed in claim 1, wherein the basic separating medium comprises a basic anion exchange resin.

5. The method as claimed in claim 4, wherein the basic anion exchange resin comprises a weak base anion exchange resin.

6. The method as claimed in claim 1, wherein the basic separating medium comprises a metal oxide.

7. The method as claimed in claim 6, wherein the metal oxide comprises one or more of activated alumina, titania, zirconia, chromia, and mixtures thereof.

8. The method as claimed in claim 6, wherein the metal oxide comprises activated alumina.

9. The method as claimed in claim 1, wherein the aldehyde mixture is contacted with the basic separating medium at a space velocity of from 1 to 10 volumes of liquid per volume of basic separating medium per hour.

10. The method as claimed in claim 1, wherein the aldehyde mixture and the basic separating medium are contacted at a temperature of from 5 to 45° C.

11. The method as claimed in claim 1, wherein the carboxylic acid comprises carbon atoms in the range of from 2 to 8.

12. The method as claimed in claim 1, wherein the carboxylic acid comprises 3-hydroxypropionic acid.

13. The method as claimed in claim 1, wherein contacting the aldehyde mixture with the basic separating medium yields a first aldehyde containing effluent comprising at least 70 percent of the aldehyde present in the aldehyde mixture.

14. The method as claimed in claim 1, wherein contacting the aldehyde mixture with the basic separating medium yields a first aldehyde containing effluent comprising at least 90 percent of the aldehyde present in the aldehyde mixture.

15. The method as claimed in claim 1, wherein the aldehyde mixture comprises 3-hydroxypropionaldehyde.

16. The method as claimed in claim 1, wherein the aldehyde mixture is dissolved in a diluent which comprises water and the carboxylic acid comprises at most 8 carbon atoms.

17. The method as claimed in claim 1, wherein the metal cation comprises a Group VIII metal cation.

18. The method as claimed in claim 1, wherein the metal cation comprises cobalt and/or rhodium cations.

19. The method as claimed in claim 1, wherein the acidic separating medium comprises a carboxylic acid cation exchange resin.

20. The method as claimed in claim 1, wherein contacting with the acidic separating medium yields a second aldehyde containing effluent comprising a total of at most 0.001 molar equivalents of the metal cation per liter of the second aldehyde containing effluent.

21. A method of treating an aqueous 3-hydroxypropionaldehyde mixture comprising 3-hydroxypropionic acid and cobalt and/or rhodium cations, which method comprises:
    contacting the aqueous 3-hydroxypropionaldehyde mixture with a weak base anion exchange resin while controlling the pH of the mixture at a value of at most 6, as measured at a temperature of operation, and
    subsequently or simultaneously contacting with a carboxylic acid cation exchange resin.

22. The method as claimed in claim 21, wherein the pH of the aqueous 3-hydroxypropionaldehyde mixture is maintained at a pH of at most 5, as measured at a temperature of operation.

23. The method as claimed in claim 21, wherein the aqueous 3-hydroxypropionaldehyde mixture is formed by oxidizing an aqueous 3-hydroxypropionaldehyde mixture comprising 3-hydroxypropionic acid, and a cobalt and/or rhodium carbonyl compound under acidic conditions at a temperature of 5 to 45° C.

24. A process for preparing a 1,3-propanediol which process comprises:
    treating a 3-hydroxypropionaldehyde mixture comprising a carboxylic acid and cobalt and/or rhodium cations, by:
    contacting the 3-hydroxypropionaldehyde mixture with a basic separating medium while controlling the pH of the 3-hydroxypropionaldehyde mixture at a value of at most 6, as measured at a temperature of operation, and
    subsequently or simultaneously contacting with an acidic separating medium; and
    hydrogenating the treated 3-hydroxypropionaldehyde mixture.

* * * * *